(12) United States Patent
Wang

(10) Patent No.: US 9,370,465 B2
(45) Date of Patent: Jun. 21, 2016

(54) SMART IV BAG WITH OPTICAL IV DRUG IDENTIFICATION TAG

(71) Applicant: BWT Property, Inc., Newark, DE (US)

(72) Inventor: Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 71 days.

(21) Appl. No.: 14/047,083

(22) Filed: Oct. 7, 2013

(65) Prior Publication Data

US 2014/0098366 A1 Apr. 10, 2014

Related U.S. Application Data

(60) Provisional application No. 61/711,291, filed on Oct. 9, 2012.

(51) Int. Cl.
| | |
|---|---|
| *A61J 1/12* | (2006.01) |
| *G01J 3/44* | (2006.01) |
| *G01J 3/42* | (2006.01) |
| *A61J 1/10* | (2006.01) |
| *G01N 21/552* | (2014.01) |
| *G01N 21/64* | (2006.01) |
| *G01N 21/65* | (2006.01) |
| *G01N 21/77* | (2006.01) |

(52) U.S. Cl.
CPC .... *A61J 1/12* (2013.01); *A61J 1/10* (2013.01); *G01J 3/42* (2013.01); *G01J 3/44* (2013.01); *G01J 3/4406* (2013.01); *G01N 21/552* (2013.01); *G01N 21/6428* (2013.01); *G01N 21/65* (2013.01); *G01N 21/77* (2013.01); *A61J 2205/20* (2013.01)

(58) Field of Classification Search
CPC ............ A61J 1/10; A61J 1/12; G01N 21/552; G01N 21/553; G01N 21/554; G01J 3/44; G01J 3/4406; G01B 21/6428; G01B 21/64; G01B 21/65
See application file for complete search history.

(56) References Cited

U.S. PATENT DOCUMENTS

| | | | |
|---|---|---|---|
| 6,070,761 A * | 6/2000 | Bloom et al. ................... 222/81 |
| 7,939,333 B2 * | 5/2011 | Geddes et al. .................. 436/97 |
| 7,952,710 B2 | 5/2011 | Flank et al. |
| 2003/0204330 A1 * | 10/2003 | Allgeyer ......................... 702/32 |
| 2004/0078219 A1 * | 4/2004 | Kaylor et al. ..................... 705/2 |
| 2007/0142777 A1 | 6/2007 | Klein |
| 2011/0198255 A1 * | 8/2011 | Baumfalk et al. .......... 206/459.1 |
| 2011/0205528 A1 * | 8/2011 | Ogawa et al. ................... 356/51 |
| 2012/0065617 A1 | 3/2012 | Matsiev et al. |
| 2012/0081703 A1 * | 4/2012 | Moskovits et al. ........... 356/301 |
| 2012/0125998 A1 | 5/2012 | Magill |

* cited by examiner

*Primary Examiner* — Kara E Geisel
*Assistant Examiner* — Dominic J Bologna

(57) ABSTRACT

This invention relates to a smart IV bag with a structurally integrated optical tag for IV drug identification and monitoring. The optical tag comprises a flow cell with a fluid channel in communication with the IV bag to sample a portion of the IV fluid onto an optical surface embedded in the flow cell. The optical surface causes a light beam to interact with the sampled IV fluid to produce a spectroscopic signal. The spectroscopic signal is then analyzed to obtain the content and concentration information of the IV fluid. Unlike traditional IV bag labels, the optical tag provides real-time, in-situ monitoring of IV fluid content and concentration, which greatly reduces the risk of mislabeling induced IV error.

11 Claims, 2 Drawing Sheets

SMART IV BAG WITH OPTICAL IV DRUG IDENTIFICATION TAG

REFERENCE TO RELATED APPLICATION

This application claims an invention which was disclosed in Provisional Patent Application No. 61/711,291, filed Oct. 9, 2012, entitled "SMART IV BAG WITH OPTICAL IV DRUG IDENTIFICATION TAG". The benefit under 35 USC §119(e) of the above mentioned United States Provisional Applications is hereby claimed, and the aforementioned applications are hereby incorporated herein by reference.

FIELD OF THE INVENTION

This invention generally relates to an IV bag, more specifically to a smart IV bag with an optical IV drug identification tag.

BACKGROUND

Intravenous (IV) therapy is the process of administering medication directly into a patient's vein. IV drug delivery is one of the most powerful routes to administer drugs. Unfortunately, it is also one of the most common reasons for medication error, accounting for up to 35 percent that result in significant harm. Common IV errors include: (a) wrong drug administered; (b) improper timing of administration; (c) wrong dosage amount; (d) improper injection of drug; (d) dangerous combination of drugs administered; and (f) defective IV pump or valve. There thus exists a need to rapidly identify and verify the chemical content of the IV fluid to ensure the correct drug and dosage to be delivered to the right patient.

SUMMARY OF THE INVENTION

It is the overall goal of the present invention to provide a smart IV bag with a structurally integrated optical tag for IV drug identification and monitoring. The optical tag comprises a flow cell with a fluid channel in communication with the IV bag to sample a portion of the IV fluid onto an optical surface embedded in the flow cell. The optical surface causes a light beam to interact with the sampled IV fluid to produce a spectroscopic signal. The spectroscopic signal is then analyzed by an optical spectrometer to obtain the content and concentration information of the IV fluid. Unlike traditional IV bag labels, the optical tag provides real-time, in-situ monitoring of IV fluid content and concentration, which greatly reduces the risk of mislabeling induced IV error.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
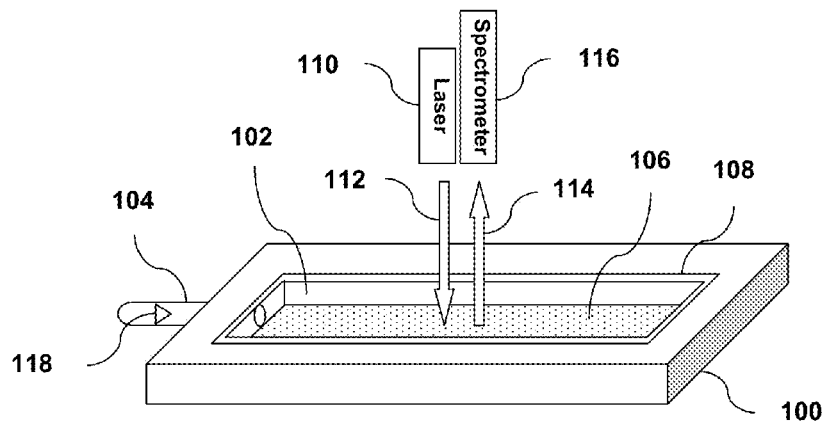
FIG. 1 illustrates one exemplary optical IV drug identification tag based on surface enhanced Raman spectroscopy (SERS)

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a smart IV bag with optical IV drug identification tag. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 illustrates one exemplary optical IV drug identification tag based on surface enhanced Raman spectroscopy (SERS). The SERS based optical tag 100 comprises a flow cell 102 with a flexible tube 104. The tube 104 can be connected to an IV bag to sample a portion of the IV fluid into the flow cell 102. A SERS active surface 106 is embedded in the flow cell 102 to receive the IV fluid sample. The SERS tag 100 further comprises a transparent window 108 for transmitting excitation light 112, preferably produced by a laser light source 110, to the SERS active surface 106. The laser light 112 excites a Raman scattering signal 114 from the IV fluid in close proximity to the SERS active surface 106. The Raman scattering signal 114 is then delivered into an optical spectrometer 116 for spectroscopic analysis. The SERS active surface 106 is preferably a roughened metal surface with nanostructures, which greatly enhance the intensity of the Raman scattering signal 114 through the excitation of surface plasmons. Other optical nano-structures such as surface gratings can be formed on the active surface 106 through a lithography process to further enhance the optical signal.

The SERS tag 100 further comprises a valve 118 mounted in the flexible tube 104, which seals the fluid channel to the flow cell 102. Before IV drug delivery, the practitioner can break open the valve 118 such that the IV fluid is delivered to the SERS active surface 106 for performing Raman spectroscopy analysis. The valve 118 can be made as a one-directional valve such that the IV fluid can only flow from the IV bag into the flow cell to avoid any possible contamination to the IV fluid. In addition, a filtration member may be embedded in the tube 104 to remove certain chemical contents of the IV fluid such that only the specific IV drug can reach the SERS active surface 106 to be measured thereof.

Figure 2:
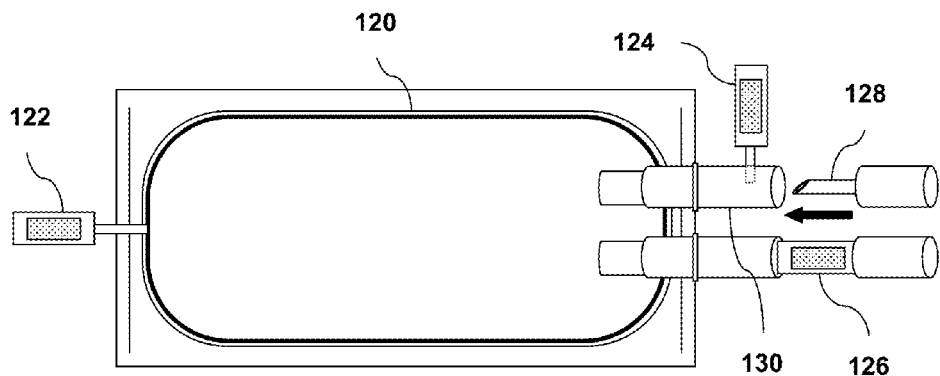
FIG. 2 illustrates a smart IV bag with structurally integrated SERS tags.

FIG. 2 illustrates a smart IV bag 120 with structurally integrated SERS tags 122, 124, and 126, all having similar construction as the SERS tag 100 in FIG. 1. In the first approach, the SERS tag 122 is connected to the bottom of the IV bag 120 through a flexible tube. The fluid channel in the flexible tube is sealed by a valve. Before IV drug delivery, the optical practitioner presses or snaps the flexible tube such that the sealing valve is broken open to lead the IV fluid to the SERS active surface. Raman spectroscopy analysis is then performed through the transparent window of the SERS tag to verify the chemical content and concentration of the IV fluid. In the second approach, a sealed SERS tag 124 is mounted at the outlet of the IV bag 120. When a needle 128 is inserted into the micro-drip tubing 130, it will break open the fluid channel to the SERS tag such that Raman spectroscopy analysis can be performed on the IV fluid. In the third approach, the SERS tag 126 comprises two flexible tubes. One functions as the input fluid channel and the other functions as the output fluid channel. Thus the SERS tag 126 can be mounted in the path of the IV fluid for continuously on-line monitoring.

The optical tag of the present invention does not perturb the IV fluid and can be used for single measurement or continuous monitoring. Unlike traditional IV bag labels, the SERS tag provides real-time, in-situ monitoring of IV fluid content and concentration. This feature greatly reduces the risk of mislabeling induced IV error.

In a slight variation of the present embodiment, the SERS active surface 106 of the optical tag 100 further comprises immobilized antibodies which can bind with a specific type of analytes in the IV fluid and bring them to the proximity of the SERS active surface 106 for performing Raman spectroscopic analysis. In addition, the SERS active surface 106 may incorporate fluorescence quenching molecules for suppressing the florescence emission of the IV drug such that a high fidelity SERS spectrum can be acquired.

Figure 3:
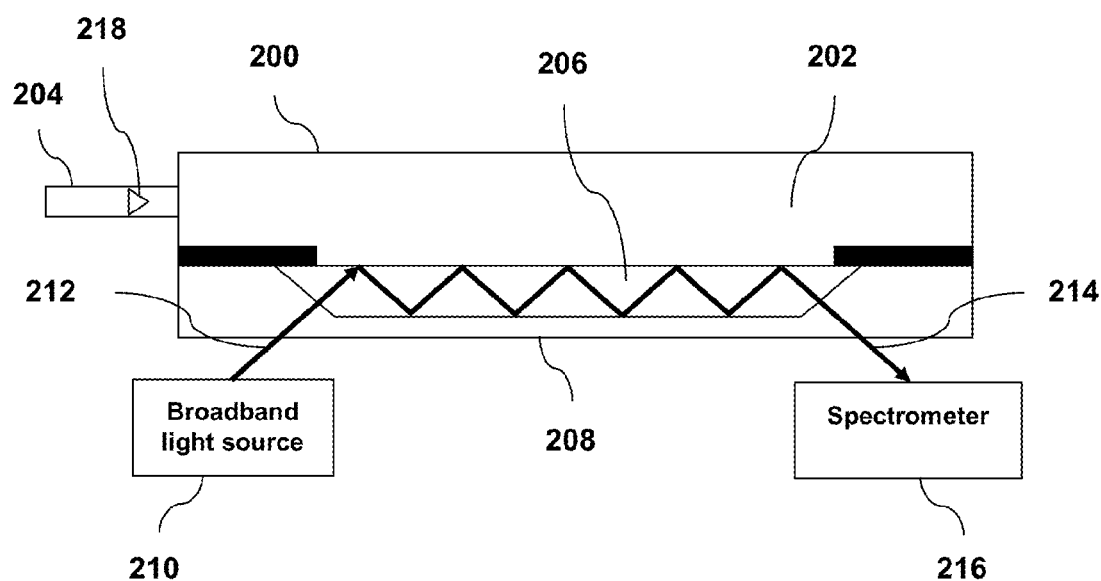
FIG. 3 illustrates another exemplary optical IV drug identification tag based on attenuated total reflection (ATR) absorption spectroscopy.

FIG. 3 illustrates another embodiment of the optical IV drug identification tag, which utilizes an attenuated total reflection (ATR) surface to measure the absorption spectrum of the IV fluid. Similar to the SERS based optical tag of FIG. 1, the ATR based optical tag 200 comprises a flow cell 202 with a flexible tube 204. The tube 204 can be connected to an IV bag to sample a portion of the IV fluid into the flow cell 202. The ATR member 206 comprises a crystal (or other high refractive index optical medium) with two parallel surfaces. One surface is exposed to the IV fluid sample. A light beam 212 from a broadband light source 210 is directed onto the ATR member 206 through a transparent window 208. The incident angle of the light beam 212 is controlled in such a way that the light beam 212 is totally internally reflected at the surface of the crystal, creating an evanescent wave that extends into the IV fluid sample in proximity to the surface of the crystal. The evanescent wave is absorbed at the absorption bands of the IV fluid. The attenuated light beam 214 is then passed through the optical window 208 to an optical spectrometer 216 for spectral analysis. The obtained absorption spectrum of the IV fluid reveals its chemical content and concentration. The light beam 212 is reflected multiple times between the two surfaces of the crystal, which greatly increases the path length of the evanescent wave in the IV fluid. This helps to increase the extinction ratio of the obtained absorption spectrum. The ATR based optical tag 200 may further comprise a valve 218 as well as a filtration member (not shown) to control the flow of the IV fluid and the chemical content of the IV fluid sample that enters the flow cell 202. The ATR tag 200 can be structurally integrated with an IV bag in similar manners as shown in FIG. 2.

In a slight variation of the present embodiment, the ATR member 206 is a modified optical waveguide such as a tapered optic fiber made of glass or plastic material. The light at the tapered region of the optical fiber propagates as an evanescent wave, which interacts with the IV fluid to produce an absorption spectrum of the IV fluid.

In yet another variation of the present invention, the optical tag comprises a fluorescence active surface, e.g. a dielectric grating deposited on a gold film to enhance a fluorescence emission of the IV fluid sample. The fluorescence spectrum of the IV fluid is then analyzed to obtain the content and concentration information of the IV drug.

In yet another variation of the present invention, the optical tag comprises an optical surface which selectively reflects certain wavelength bands in the optical spectrum for facilitating the trans-reflectance or absorption spectrum measurement of the IV fluid.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An intravenous (IV) fluid container with pre-filled IV fluid for IV therapy, said IV fluid container comprising a structurally integrated optical IV drug identification tag, said optical IV drug identification tag comprising:
   a flow cell with a fluid channel in communication with said IV fluid container;
   a one-directional breakable valve embedded in said fluid channel for sealing said fluid channel to said flow cell, said one-directional breakable valve is configured to allow a portion of the IV fluid to flow one-directionally from said IV fluid container into said flow cell when broke open; and
   a surface enhanced Raman spectroscopy (SERS) active surface embedded in said flow cell, said SERS active surface is configured to receive said portion of the IV fluid and cause a light beam to interact with said portion of the IV fluid to produce a Raman scattering signal containing a content and concentration information of the IV fluid.

2. The IV fluid container of claim 1, wherein said optical IV drug identification tag further comprising a transparent window for transmitting said light beam to said SERS active surface.

3. The IV fluid container of claim 1, wherein said SERS active surface comprises a roughened metal surface with nanostructures.

4. The IV fluid container of claim 3, wherein said nanostructures comprise surface gratings.

5. The IV fluid container of claim 1, wherein said optical IV drug identification tag further comprising a filtration member embedded in said fluid channel, said filtration member is configured to remove a pre-determined content of the IV fluid.

6. A method for identifying and monitoring the content and concentration of intravenous (IV) fluid in an IV fluid container, the method comprising the steps of:

provided an optical IV drug identification tag structurally integrated with the IV fluid container, said optical IV drug identification tag comprising a flow cell with a fluid channel in communication with said IV fluid container, a one-directional breakable valve embedded in said fluid channel for sealing said fluid channel to said flow cell, said one-directional breakable valve is configured to allow a portion of the IV fluid to flow one-directionally from said IV fluid container into said flow cell when broke open, and a surface enhanced Raman spectroscopy (SERS) active surface embedded in said flow cell to receive said portion of the IV fluid;

causing a light beam to interact with said portion of the IV fluid in proximity to said SERS active surface to produce a Raman scattering signal; and measuring said Raman scattering signal to obtain a content and concentration information of the IV fluid.

7. The method of claim 6, wherein said optical IV drug identification tag further comprising a transparent window for transmitting said light beam to said SERS active surface.

8. The method of claim 6, wherein said optical IV drug identification tag further comprising a filtration member embedded in said fluid channel, said filtration member is configured to remove a pre-determined content of the IV fluid.

9. An intravenous (IV) fluid container with pre-filled IV fluid for IV therapy, said IV fluid container comprising a structurally integrated optical IV drug identification tag, said optical IV drug identification tag comprising:

a flow cell with a fluid channel in communication with said IV fluid container;

a one-directional breakable valve embedded in said fluid channel for sealing said fluid channel to said flow cell, said one-directional breakable valve is configured to allow a portion of the IV fluid to flow one-directionally from said IV fluid container into said flow cell when broke open; and a fluorescence active surface embedded in said flow cell, said fluorescence active surface is configured to receive said portion of the IV fluid and cause a light beam to interact with said portion of the IV fluid to produce a fluorescence signal containing a content and concentration information of the IV fluid.

10. The IV fluid container of claim 9, wherein said fluorescence active surface comprises a dielectric grating deposited on a gold film.

11. The IV fluid container of claim 9, wherein said optical IV drug identification tag further comprising a filtration member embedded in said fluid channel, said filtration member is configured to remove a pre-determined content of the IV fluid.

* * * * *